United States Patent [19]

Krueger, Jr. et al.

[11] Patent Number: 5,365,066

[45] Date of Patent: Nov. 15, 1994

[54] LOW COST MEANS FOR INCREASING MEASUREMENT SENSITIVITY IN LED/IRED NEAR-INFRARED INSTRUMENTS

[75] Inventors: Don E. Krueger, Jr., McLean, Va.; Robert D. Rosenthal, Gaithersburg, Md.

[73] Assignee: Futrex, Inc., Gaithersburg, Md.

[21] Appl. No.: 980,272

[22] Filed: Nov. 23, 1992

Related U.S. Application Data

[63] Continuation-in-part of Ser. No. 813,739, Dec. 30, 1991, Pat. No. 5,237,178, which is a continuation-in-part of Ser. No. 565,302, Aug. 10, 1990, Pat. No. 5,077,476, which is a continuation-in-part of Ser. No. 544,580, Jun. 27, 1990, Pat. No. 5,086,299, which is a continuation-in-part of Ser. No. 298,904, Jan. 19, 1989, Pat. No. 5,028,787.

[51] Int. Cl.$^5$ .............................................. G01N 21/35
[52] U.S. Cl. .............................. 250/341.2; 250/339.01; 356/39; 128/633
[58] Field of Search ............................ 250/341, 252.1, 339, 250/343, 346; 356/39; 128/633

[56] References Cited

U.S. PATENT DOCUMENTS 5,077,476  12/1991  Rosenthal ........................... 250/341
5,204,532  4/1993  Rosenthal ........................... 250/341

*Primary Examiner*—Paul M. Dzierzynski
*Assistant Examiner*—Richard Hanig
*Attorney, Agent, or Firm*—Rothwell, Figg, Ernst & Kurz

[57] ABSTRACT

A low cost means for increasing measurement sensitivity in LED near-infrared instruments is disclosed which utilizes a current modification means for modifying the driving current supplied to each IRED as a function of the opacity of the particular sample being measured. The current modification means is part of the processing means and comprises means for measuring a signal level for each IRED at an analog-to-digital converter. Based upon the signal level detected for each IRED, the current modification means modifies the current to each IRED to a value that is as high as possible without saturating the analog-to-digital converter. Thus, by modifying the driving current of each IRED to such a maximal value, the analytical instrument of the present invention provides high resolution without the use of expensive electronic circuitry. Also provided is a system for generating and storing an optical signature of a particular user, thus further insuring the accuracy of measurements taken by the instrument.

21 Claims, 8 Drawing Sheets

LOW COST MEANS FOR INCREASING MEASUREMENT SENSITIVITY IN LED/IRED NEAR-INFRARED INSTRUMENTS

CROSS-REFERENCE TO RELATED APPLICATION

This application is a continuation-in-part of co-pending application Ser. No. 07/813,739, U.S. Pat. No. 5,237,178 filed on Dec. 30, 1991, which is a continuation-in-part of Ser. No. 07/565,302, U.S. Pat. No. 5,077,476 filed on Aug. 10, 1990, which is a continuation-in-part of application Ser. No. 07/544,580, filed Jun. 27, 1990, U.S. Pat. No 5,086,299 which is a continuation-in-part of application Ser. No. 07/298,787, filed Jan. 19, 1989, U.S. Pat. No. 5,028,787.

BACKGROUND OF THE INVENTION

1. Field of the Invention

This invention relates to instruments for the non-invasive quantitative measurement of constituents in a product, such as protein in wheat or blood glucose levels in an individual's blood. Specifically, this invention relates to LED/IRED near-infrared instruments having improved measurement sensitivity.

2. DESCRIPTION OF THE BACKGROUND ART

Since the early 1970's, near-infrared quantitative measuring instruments have become widely used in agricultural applications. Such instruments have proven to provide highly accurate quantitative and qualitative measurements of chemical constituents for a wide range of products.

An example of these near-infrared quantitative measuring instruments having agricultural application is the TREBOR-90XL grain analyzer. The TREBOR-90XL is a near-infrared diffuse transmittance instrument which provides highly accurate quantitative measurements, such as moisture content in grain.

Near-infrared quantitative analysis instruments have also been used to obtain information concerning the chemical composition of blood. This information has been used to assess the health characteristics of both people and animals. For example, analysis of the glucose content of blood provides an indication of the current status of metabolism. Blood analysis, by the detection of above or below normal levels of various substances, also provides a direct indication of the presence of certain types of diseases and dysfunctions.

A current type of blood glucose analytical instrumentation has been developed which non-invasively measures blood glucose levels in individual users. A near-infrared quantitative analysis instrument of this type is described in U.S. Pat. No. 5,077,476 (Rosenthal). The non-invasive blood glucose measurement instrument analyzes near-infrared energy following interactance with venous or arterial blood, or transmission through a blood-containing body part. The instrument measures a change in light absorption that occurs, in part, due to the glucose content of the blood stream.

Non-invasive measurement instruments of this type have broad applications for the diabetic community. For example, people with diabetes have wide changes in their blood glucose content during the day which often require multiple measurements per day for good disease control. The ability to make these near-infrared blood glucose level measurements non-invasively means that more measurements will likely be made per day than would be made using the more painful blood drawing approach.

The near-infrared quantitative measurement instruments discussed above both require the capability to take measurements over a broad range of light levels. For example, measurements are taken of highly transparent materials, i.e. where the Log 1/T value is near zero, and measurements are taken of nearly opaque materials, i.e. those having a Log 1/T values approaching 7.0.

The commercial near-infrared analysis instruments have essentially used two different techniques to perform such low light measurements over a broad optical range. A first technique involves having the detector signal linearly amplified and then converted to a logarithmic function by means of a logarithmic amplifier. The output of the logarithmic amplifier is then converted to a digital signal via an analog-to-digital ("A/D") converter for entry into the microprocessor built into the instrument. An alternative approach involves omitting the expensive logarithmic amplifier, which normally has undesirable nonlinearity characteristics, and using a higher resolution A/D converter, i.e. an A/D converter having a significant number of additional "bits" of resolution, in order to provide the requisite data resolution for the microprocessor.

For example, a 12 bit A/D is used if the signal is first modified by a logarithmic amplifier. If there is no logarithmic amplifier, typically a 16 bit A/D converter is used. However, instruments utilizing the logarithmic amplifiers or high resolution A/D converters increase the instrument's overall cost. Specifically, logarithmic amplifiers, such as Analog Devices, Inc. model 755N, cost in excess of $80. Likewise, the difference in cost between a high speed 12 bit and a 16 bit A/D converter can be in approximately the same price class.

Thus, there is a great need for a near-infrared measurement instrument which provides the resolution necessary for precision measurement using near-infrared techniques but without the expensive electronic circuitry currently necessary to achieve high resolution measurements.

There is also a need, as the calibration of near-IR instruments becomes customized for an individual subject, to ensure that the instrument is being used to analyze only the subject for whom (which) it has been calibrated.

SUMMARY OF THE INVENTION

In accordance with the present invention, a near-infrared quantitative analysis instrument for measuring a constituent in a sample is disclosed which comprises a current modification means for modifying the driving current supplied to each IRED as a function of the opacity of the particular sample being measured. In one embodiment, a near-infrared quantitative analysis instrument for measuring a blood analyte present in the blood utilizes the current modification means to modify the driving current supplied to each IRED as a function of the opacity of the particular individual's body part being measured. The current modification means is part of the processing means and comprises means for measuring a signal at the A/D converter for each IRED which represents the energy emerging through the individual user's body part. Based upon this signal detected for each IRED, the current modification means modifies the current to each IRED to be as high as possible without saturating the A/D converter.

By modifying the driving current to each IRED as high as possible without saturating the A/D converter, the analytical instrument of the present invention provides high resolution without the use of expensive electronic circuitry.

In accordance with another aspect of the invention, an analytical instrument is provided which enables IRED current modifications to be made in an energy efficient manner. The analytical instrument utilizes a finger insert which, inter alia, enables an optical transmission spectra unique to the individual user to be measured and stored. While the multiple measurements of the individual's transmission spectra are being generated, the driving currents to the IRED can be established which eliminates the need to reset the IRED levels each time the instrument is used.

In accordance with another embodiment of the present invention, a near-infrared apparatus for determining percent fat in a body is disclosed which utilizes a current modification means for modifying the driving current to each IRED as a function of the body part being measured. Also, a near-infrared instrument for measuring a constituent present in a sample, such as the protein content in wheat, which utilizes the current modification means of the present invention.

In accordance with yet another aspect of the invention, a near-IR analysis instrument includes a security means for ensuring that, within acceptable margins of error, only the particular user for whom it has been calibrated can use it to conduct analytical procedures.

DETAILED DESCRIPTION OF THE PREFERRED EMBODIMENTS

Near-infrared quantitative measurement instruments which utilize IREDs and LEDs have an advantageous feature in that they are able to be switched on and off at high speed. As such, a desired spectrum scan can be achieved with these near-infrared instruments by first, properly selecting the LEDs/IREDs and their accompanying optical bandpass filters, and then, sequentially illuminating each of the LED/IREDs to provide the optical measurement at that wavelength.

Figure 1:
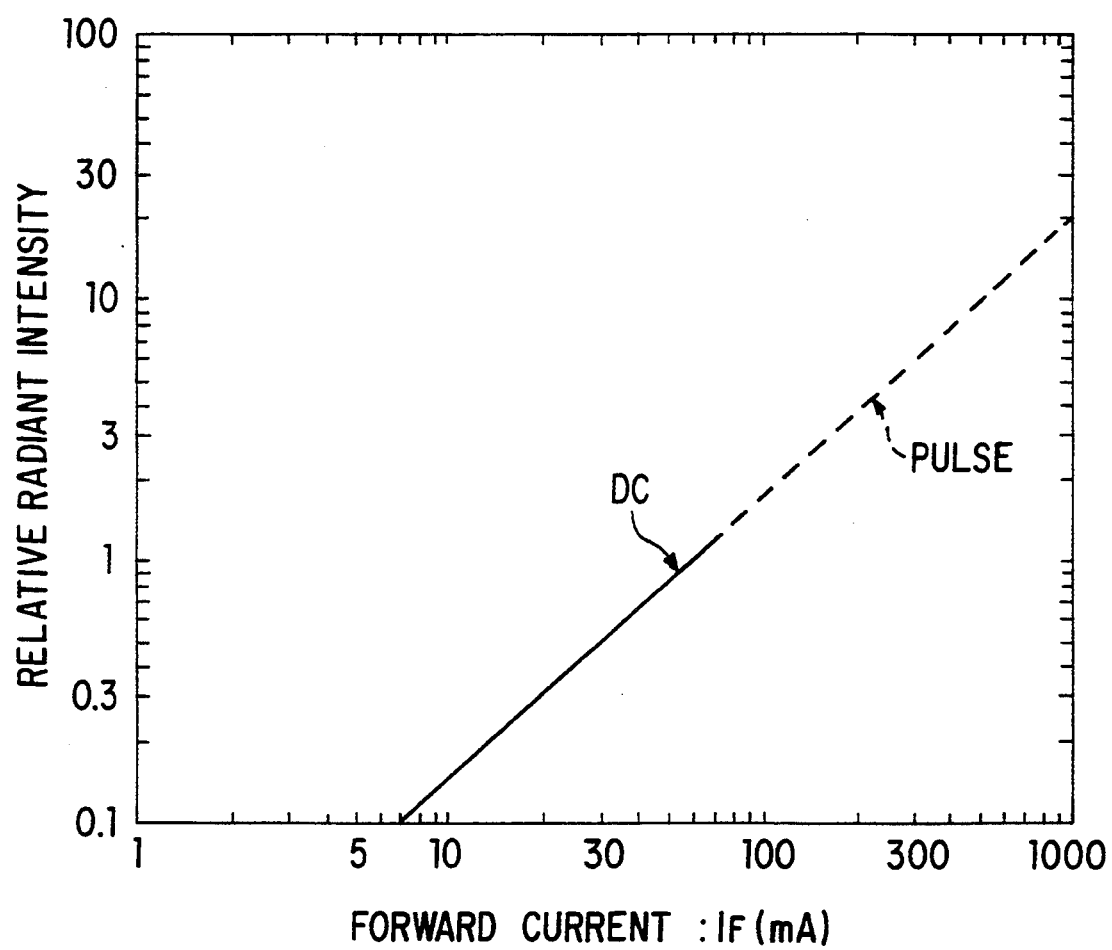
FIG. 1 is a graph illustrating the relative radiant intensity of an IRED versus the forward current driving the IRED.

FIG. 1 illustrates another favorable characteristic of LED/IREDs which is that the amount of light output is essentially proportional to the amount of current driving the LED/IRED. Thus, by increasing the driving current to the LED/IRED illumination system, the optical energy output from the LED/IRED is increased linearly without adding any noise to the detector signal. Increasing the light output of an optical system can be advantageous because such an approach allows more detector sensitivity, although it can cause saturation of the detector circuitry on very transparent samples.

The driving current value for LED/IREDs which are used in near-infrared instruments is typically preset at the factory. The driving current value is typically selected such that each LED/IRED will not saturate the capability of an optical detector circuitry for the most transparent sample intended to be measured by that instrument. For example, most natural materials, such as wheat, have a wide range of opacity. Thus, at a particular wavelength, different wheat samples can have a difference in percent transmission ranging from as much as ten to one. Similarly, differences in race, size and body composition result in significant variations in opacity of individuals' fingers. Since it is mandatory to be able to measure both the more transparent sample and the highly opaque samples, the selection of the LED/IRED current based on the most transparent sample causes very low, and potentially undesirable, detector signal levels when measuring more opaque samples.

Thus, in accordance with present invention, a near-infrared quantitative analysis instrument is disclosed which instead of utilizing IREDs having preselected driving currents, comprises a current modification means for modifying the driving current supplied to each IRED as a function of the opacity of the particular sample being measured. By regulating the current to each IRED, high resolution measurements are provided in a low-cost near-infrared analytical instrument.

Figure 2:
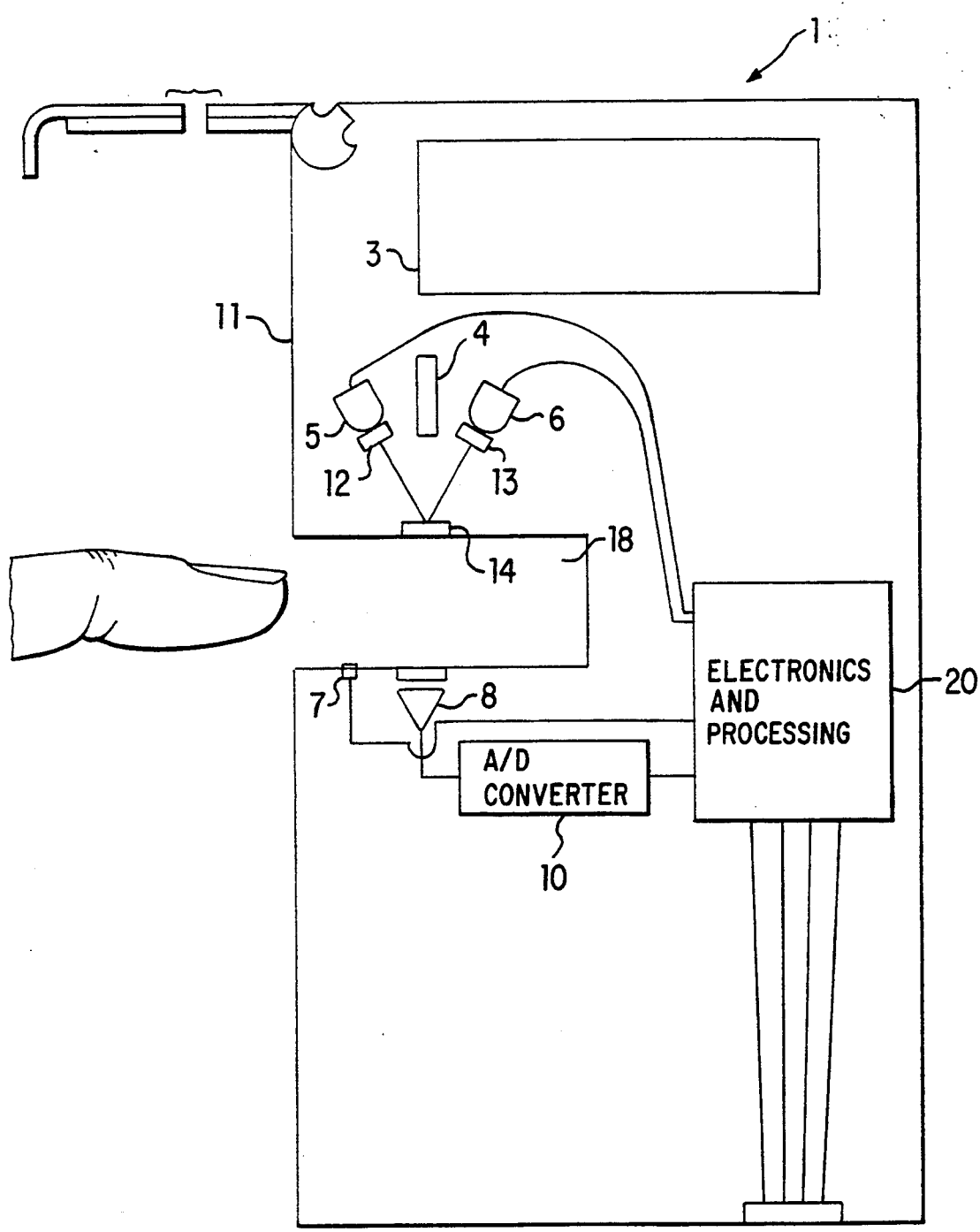
FIG. 2 illustrates a non-invasive glucose measurement instrument according to one embodiment of the present invention.

FIG. 2 illustrates one application of the present invention in a non-invasive near-infrared quantitative analysis instrument 1 which is designed to measure a blood analyte using near-infrared transmission through a test subject's body part, such as a finger. The analytical instrument 1 contains an introducing means including at least one near-infrared energy source for introducing near-infrared energy into the test subject's finger. In one embodiment of the present invention, the introducing means comprises up to twelve or more near-infrared point sources (near-infrared IRED's). IREDs 5 and 6 are shown for illustrative purposes in FIG. 2. In a preferred embodiment, the IREDs emit energy in the range of approximately 600 nanometers to approximately 1100 nanometers.

The analytical instrument also utilizes a detector circuit means for detecting near-infrared energy emerging from the test subject's body part and producing a signal representative of the energy emerging from the individual's body part. The detector circuit means comprises detector 8 and A/D converter 10 as shown in FIG. 2. The detector 8 is electrically connected to the A/D converter which is electrically connected to the processing means 25 (see FIG. 3) which, according to its programming, processes the signal produced by the detector 8 and the A/D converter into a signal indicative of the quantity of blood analyte present in the test subject's blood. This information is displayed on display 3. The analytical instrument 1 calculates the quantity of blood analyte present in the test subject's blood substantially as disclosed in U.S. Pat. No. 5,077,476, incorporated herein by reference.

The analog-to-digital converter used in a preferred embodiment of the present invention is a 12 bit A/D converter. Any suitable 12-bit A/D converter can be utilized, such as the A/D converter manufactured by Analog Devices No. AD7880BR.

Illustrative IREDs 5 and 6 are separated by light baffle 4 and are positioned so that the near-infrared energy is directed through window 14, which may be light scattering, and onto the test subject's skin. Window 14, however, is an optional component and is provided as a preferred embodiment. Optical filters, illustrated at 12 and 13, are positioned between each IRED and the window 14 for filtering the near-infrared light, thereby optimizing the band of near-infrared light striking the subject.

The analytical instrument 1 utilizes a current modification means for modifying the driving current supplied to each IRED as a function of the opacity of the particular sample being measured. The current modification means, illustrated in FIG. 3, comprises the processing means 25 and comprises means for measuring an A/D conversion value for each IRED, which represents the energy emerging from the individual's body part. Based upon the A/D conversion value detected for each IRED, the current modification means modifies the current to each IRED to be as high as possible without saturating the analog-to-digital converter. The saturation level of each A/D converter is a known value. This information is programmed into the current modification means to provide the upper reference point by which the current to an individual IRED is modified.

Figure 3:
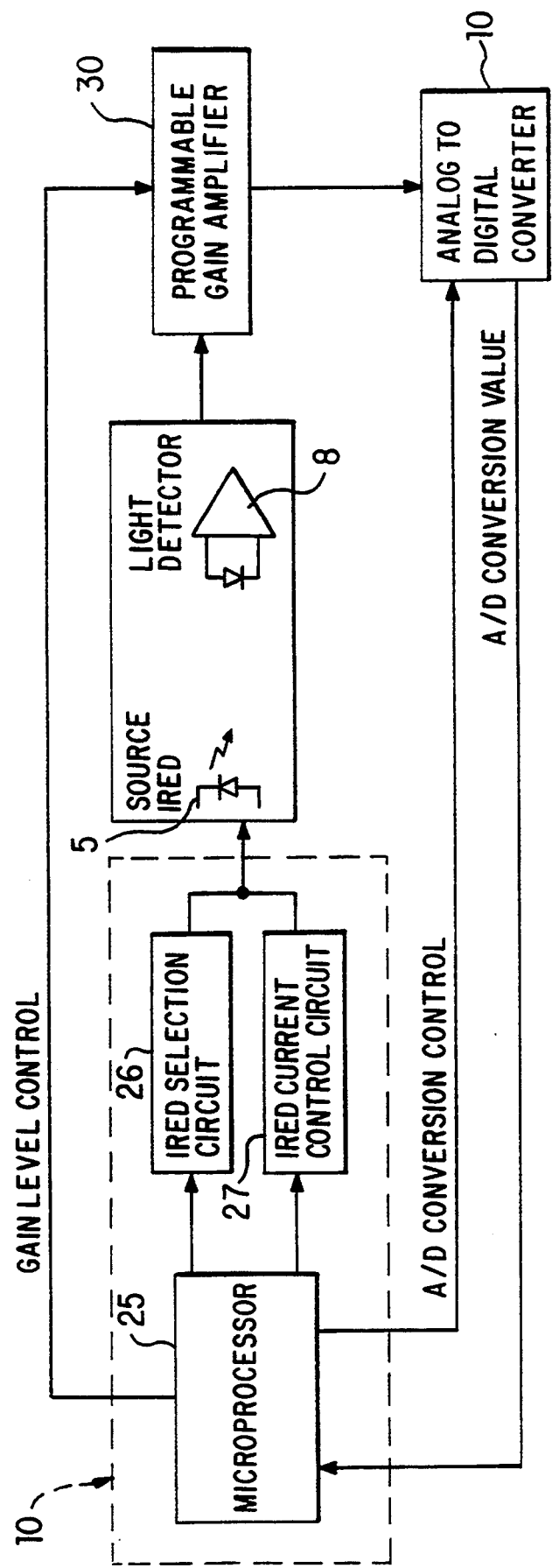
FIG. 3 is a block diagram of the IRED current modification circuitry in accordance with one embodiment of the present invention.

FIG. 3 illustrates, in a preferred embodiment, how the current modification means modifies the current to the individual IREDs based on the opacity of the sample. The current modification means 20 comprises an IRED selection circuit 26 which enables the IREDs to be sequentially energized. A programmable gain amplifier 30 is provided to amplify the signal from detector 8 and input the signal to A/D converter 10. The A/D converter 10 produces A/D conversion values which are input into the processing means 25. The processing means 25 compares the A/D conversion values with the known saturation value for the specific A/D converter. If the A/D conversion values are below the known saturation value for the A/D converter, an IRED current control circuit 27 is caused to increase the current to the specific IRED by an amount, preferably, which increases the A/D conversion values to a point just below its known saturation values.

For example, in accordance with one embodiment of the present invention, an individual's finger is exposed to energy from an IRED which is operated at 30 milliamps and produces a signal from the detector circuit means which is the equivalent of one volt. Based on the known saturation value of the A/D converter, the desired signal level from the detector circuit means for all IREDs is determined to be five volts. Thus, the current modification means then increases the driving current to the IRED to achieve a detector circuit means output of five volts, i.e. increasing the LED/IRED current by a factor of five. Alternatively, the LED/IRED current is increased until the maximum allowable LED/IRED current is reached. See FIG. 1 for illustration of typical IRED current versus light output values.

Figure 4:
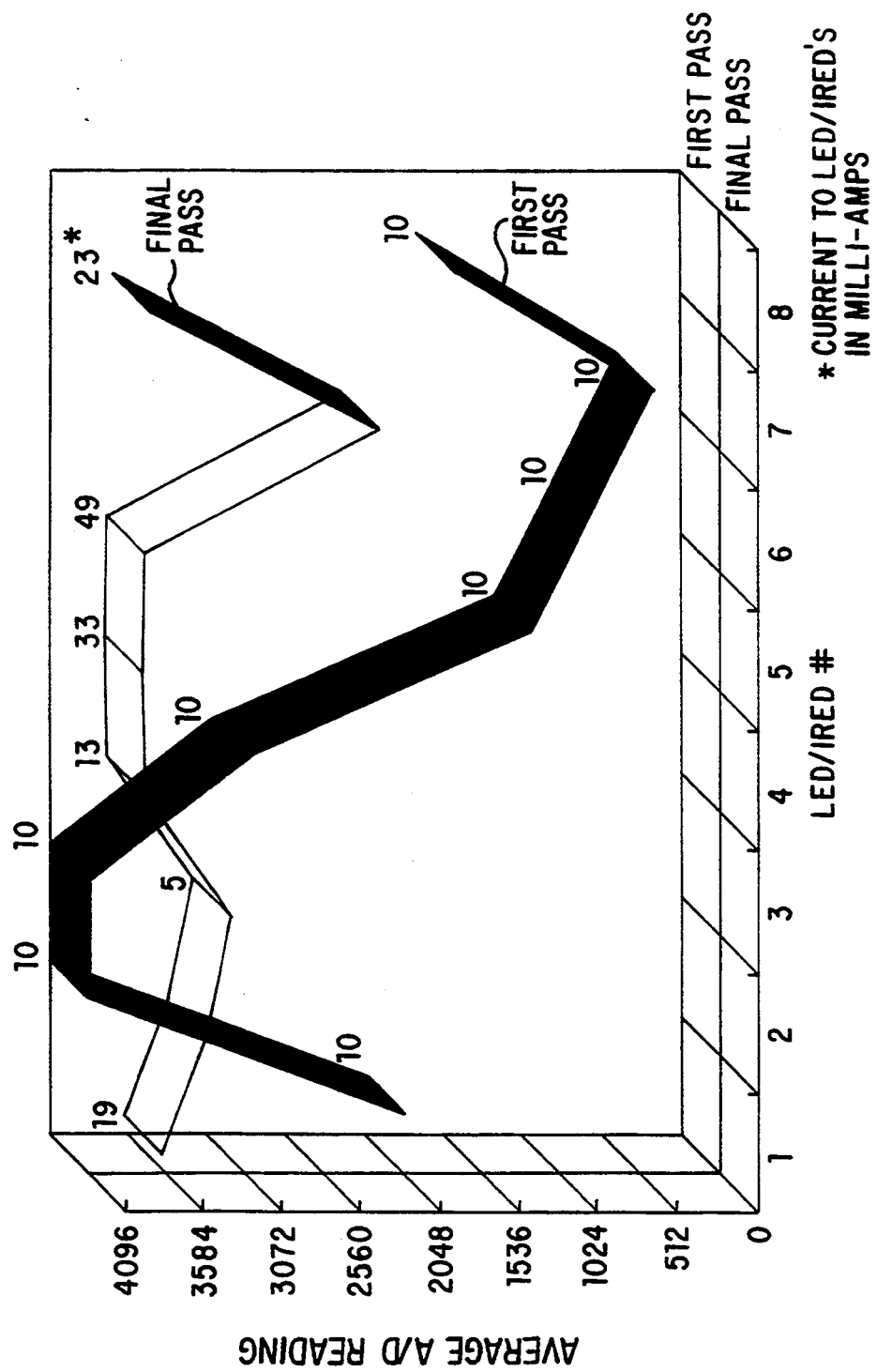
FIG. 4 is a graph illustrating average analog-to-digital readings with different current levels for each IRED in accordance with one embodiment of the present invention.

Operation of the analytical instrument in accordance with a preferred embodiment of the invention will be described in connection with the figures discussed above and FIG. 4 which shows average A/D values for the individual IREDs with different current levels. During an initial setup operation of the analytical instrument, a standardization reading is made with an empty chamber to determine the maximum current for each IRED which will not saturate the A/D converter. These values are stored in the processing means 25.

An individual's body part, i.e. finger, is then inserted into the instrument. The programmable gain amplifier is set, preferably at a medium setting, i.e. at 32. One scan is made through the finger with the IRED currents set to the maximum allowed in the current table. See FIG. 1. The A/D conversion value is examined for each IRED and the driving currents are modified as discussed above. In one embodiment, if the A/D count is between approximately ¾ to approximately 15/16 of the full A/D scale, the gain at the programmable gain amplifier is not changed and the current is left at its maximum table value. If the A/D conversion value is saturated, i.e. 4.2 volts in this embodiment, the gain is set to low, i.e. 1. In this event, a second scan is made of the finger. The current level is calculated assuming the gain to be 32 and the current level is set accordingly. If the A/D and conversion value is between 15/16 and ¾, the current is calculated for the high gain to bring it within approximately 15/16 of the full scale at high gain. In this event, the gain is set to 320 and the current is set to the calculated value.

By performing the above for every individual IRED, the particular finger being measured has the optimum optical energy for that finger or, in other words, the detector signal has the highest permissible resolution.

After performing the near-infrared measurement with the IRED current modifications as discussed above, an empty chamber measurement is made with the same modified LED/IRED levels. This measurement provides a standardization value. The actual Log 1/T value upon which the blood analyte concentration is measured is the difference between the Log 1/T value when the finger is measured at a particular wavelength and the Log 1/T value of empty chamber measurement at that same wavelength. Based upon these values, the processing means can calculate the blood analyte concentration for the individual user.

The LED/IREDs utilized in the analytical instrument of the present invention can be any suitable LED/IREDs which do not have a preset energy level and are capable of having their driving current modified. For example, such IREDs are manufactured by the Stanley Electric Company. The detector means illustrated by detector 8 in FIG. 2 can be any suitable optical detector, such as the optical detector manufactured by Hamamatsu. The programmable gain amplifier can be any suitable amplifier, such as an NEC uPC358G2.

In a preferred embodiment, the current modification means includes a suitable microprocessor, such as the one manufactured by Hitachi No. HD63A03Y. Also, the IRED current control circuit can be any suitable D/A current driver, such as the Current Driver D/A Converter manufactured by Texas Instruments, Part Number TLC7524CNS.

By controlling the current supplied to the IREDs via the current modification means, the analytical instrument of the present invention effectively provides additional resolution over and above what is normally achieved using the 12-bit A/D converter. The combination of the variable IRED current coupled with the 12-bit A/D converter effectively yields the ability of a 16-bit A/D converter. Thus, the analytical instrument of the present invention can provide high resolution without the added expense of logarithmic amplifiers or more expensive A/D converters.

Figure 5:
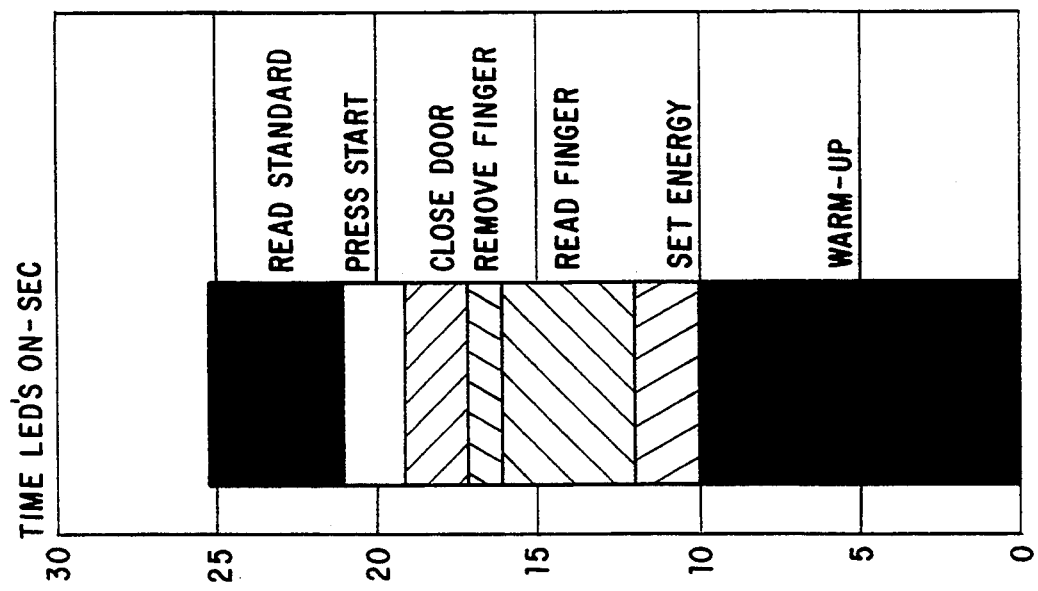
FIG. 5 illustrates the IRED power requirement to provide a near-infrared quantitative measurement in accordance with one embodiment of the present invention.

As illustrated in FIG. 2, the analytical instrument of the present invention describes a low-cost, light-weight, hand-held, battery powered unit. As such, the drain on the battery power must be carefully considered. FIG. 5 illustrates the amount of time the IREDs must be left on in order to obtain a blood analyte measurement. One potential limitation to this measurement approach is that it requires the individual user to remove his or her finger and then measure the optical standard. If any delay is made in making the standard measurement, the instrument's battery power continues to be consumed. However, the analytical instrument of the present invention protects against unlimited battery delay by providing an energy conservation means for shutting off the instruments microprocessor if the measurement has not been completed within a predetermined time period. In a preferred embodiment, the energy conservation means shuts off the microprocessor if the user does not complete the measurement within one minute.

Figure 6:
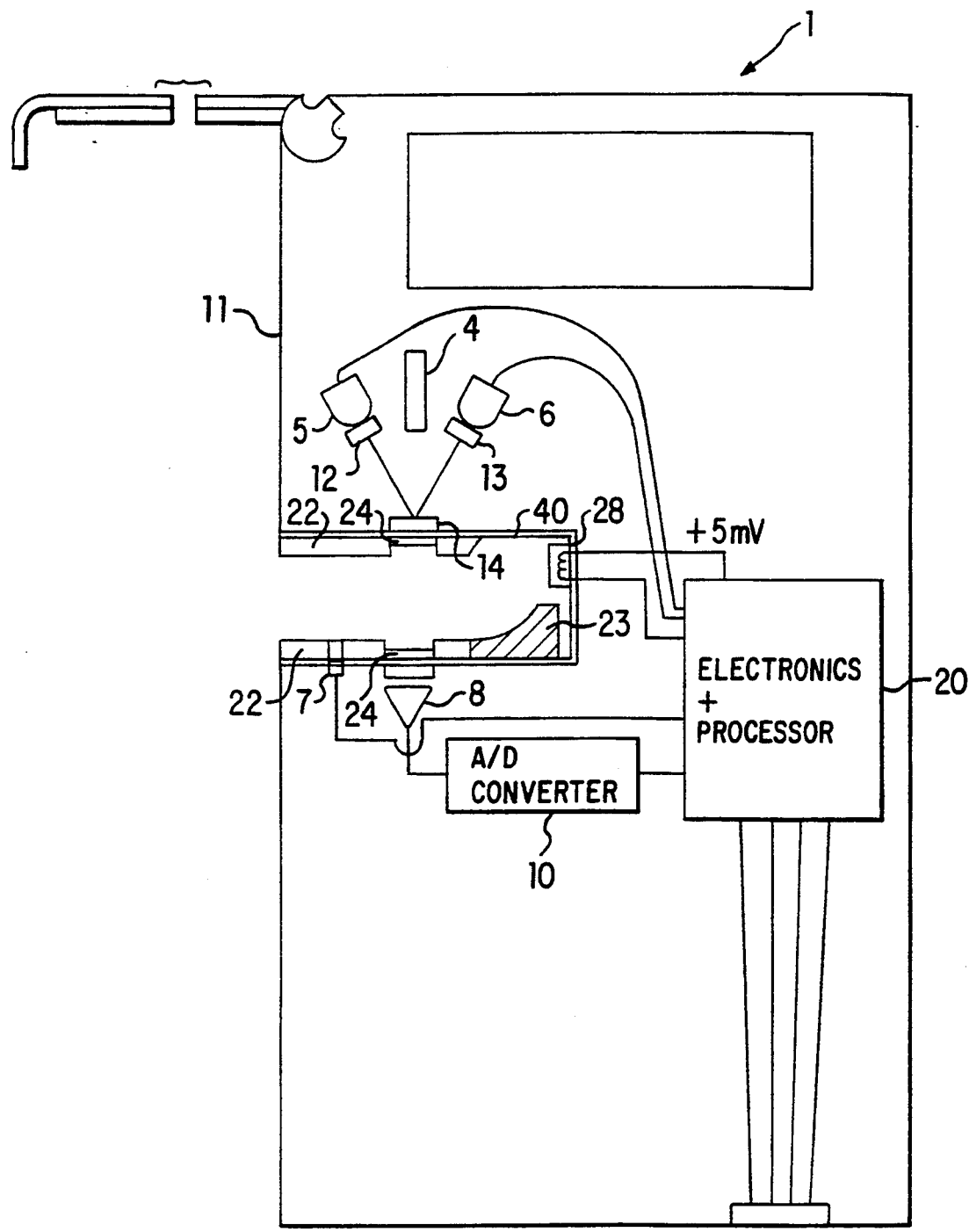
FIG. 6 illustrates a non-invasive glucose measurement instrument according to a second embodiment of the present invention.

In accordance with another embodiment of the present invention, FIG. 6 discloses an analytical instrument which enables IRED current modifications to be made in an energy efficient manner. The analytical instrument contains an introducing means, detection means and the current modification means as described above and operates substantially identically as the instrument of FIG. 2. The analytical instrument also includes a finger insert 40 which is disclosed in co-pending patent application Ser. No. 07/813,739, incorporated herein by reference.

The insert means 40 permits proper positioning of an individual's body part inside the analysis instrument 1. Another function of the insert means is to ensure that only a single individual uses a particular instrument for measurement. This function is accomplished by having the individual user insert his or her finger into the instrument and having multiple measurements, e.g. 8-10, taken in succession. This process is performed only once during the usable life of the finger insert, i.e. approximately one month, and when that finger insert is first used by the individual. These multiple measurements are stored by the instrument and provide information regarding the individual's optical transmission spectra, or "optical signature", to identify whether or not the instrument is calibrated for that particular individual. This feature requires that the individual's optical transmission spectra must match the information stored in the instrument, within a predetermined percentage of accuracy, i.e. five percent, before the instrument will operate.

A relatively simple approach to ensuring that the instrument is used only by the user for whom it has been calibrated, as mentioned above, involves storing the results of a plurality of measurements within the electronics of the instrument. For example, a series of extinction readings can be taken in the ranges of approximately 600-658 nm (a region of the near-IR band that is sensitive to skin color and blood oxygen saturation) and approximately 658-746 (a region sensitive to the combination of skin color, oxygen saturation of the blood and hemoglobin level of the blood). The stored results ("optical signature") of these readings can be compared to readings obtained when the unit is used, i.e. a "real time" optical signature, so that analysis will be performed only if the stored "optical signature" positively compares to the signature revealed by the present user.

To illustrate the utility of this approach, ten optical scans were performed on the index finger of a test subject using an instrument as described herein. The instrument included fourteen IRED's with optical filters and provided fourteen log 1/T values at specific wavelengths between 604 and 990 nm. For each of the ten scans, the following were calculated:

Slope 1=(Log 1/T)604nm−(Log 1/T)658nm

Slope 2=(Log 1/T)658nm−(Log 1/T)746nm

An average Slope 1 and Slope 2 were calculated, along with their standard deviations. From these results, 95% limits were established for an optical signature based on Slope 1 and Slope 2 by adding and subtracting twice the standard deviation from the averages.

The performance of a large (508) number of optical scans upon one subject, and scans from 267 different subjects, revealed the overall accuracy of this approach to prevent an incorrect subject from using a previously calibrated unit. Other approaches for comparing optical data from a present user to data previously stored from an initial user will be apparent to those skilled in this field.

In accordance with the present invention, the IRED current modification is made in an energy efficient manner by establishing the IRED driving currents at the same time the optical signature, i.e. optical transmission identification, is being identified. In other words, while the multiple measurements of the individual's transmission spectra are being generated, the driving currents to the IRED are established, as described above. This feature is advantageous in that it would eliminate the need to reset the IRED levels each time the instrument is used. It would also allow the IRED levels to remain at a constant value throughout the life of the finger insert which, preferably, is approximately one month.

Figure 7:
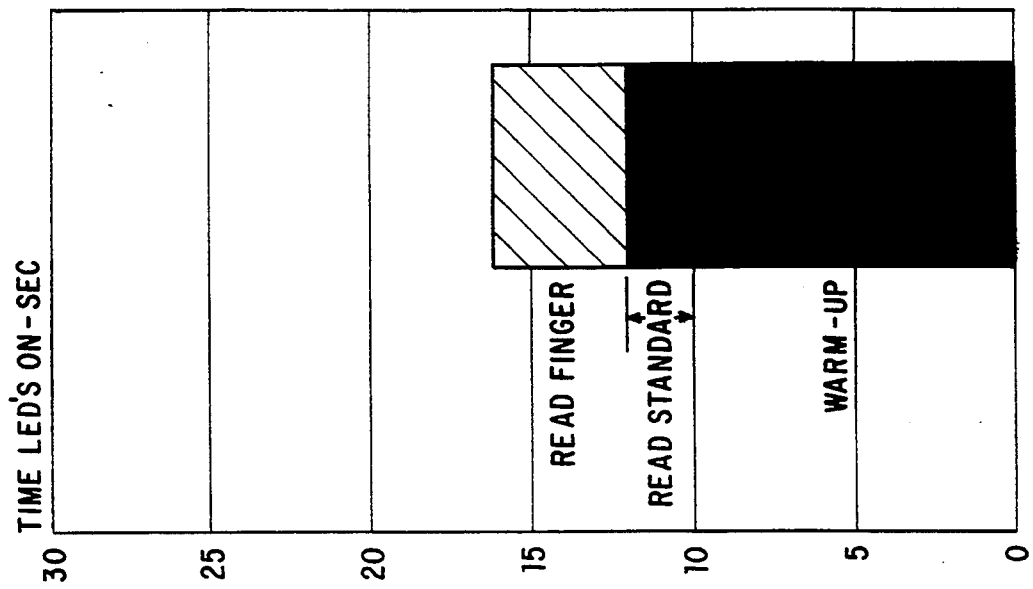
FIG. 7 illustrates the IRED power requirement to provide a near-infrared quantitative measurement in accordance with a second embodiment of the present invention.

FIG. 7 illustrates the LED/IRED power drain time that would occur by establishing IRED drive currents during the individual transmission spectra measurements. The energy saving compared to the approach illustrated in FIG. 5 is highly significant for a battery operated unit. Moreover, it eliminates any need for delays in measuring the standard, i.e. empty chamber measurement. In this case, the standard would actually be measured automatically at the end of the normal "warm-up time" that the instrument requires each time it is turned on. The net result is that it eliminates the need for the operator to first make the measurement of his or her finger and then press a separate button and make the measurement of the optical standard. Thus, only one push button would be required for operation of the instrument, i.e. to turn it on. Once the unit is turned on, the instrument will automatically warm up, measure the empty chamber and indicate to the operator to insert the operator's finger.

Once the finger is inserted, the instrument will sense that the signal at the detector has been greatly diminished. The instrument gain would then be automatically changed and the optical data read. This entire sequence, after the warm-up cycle, could be completed in less than five seconds.

Figure 8:
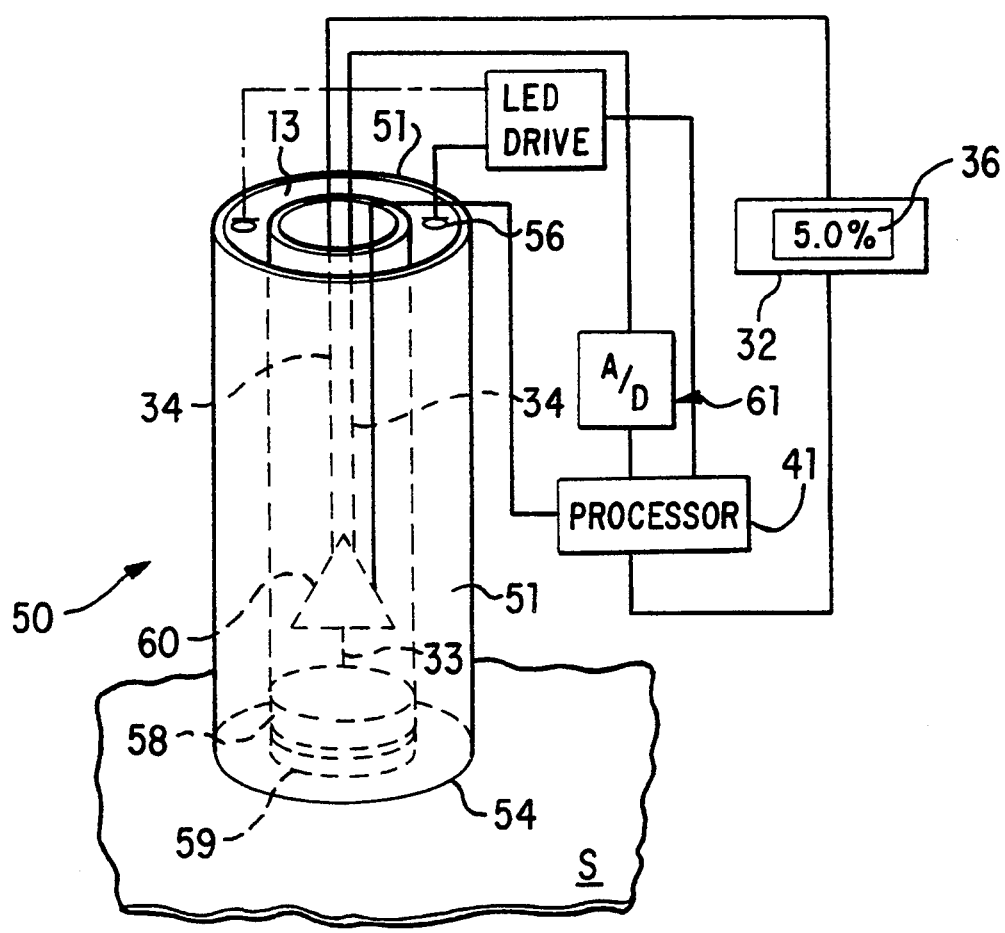
FIG. 8 illustrates a near-infrared apparatus for determining percent body fat in a body in accordance with another embodiment of the present invention.

In accordance with another embodiment of the present invention, FIG. 8 discloses a near-infrared apparatus for determining percent body fat in a body which comprises the current modification means of the present invention. The near-infrared instrument comprises a probe portion 50 which has a hollow cylindrical form and includes a hollow tubular member 51 having a wall of solid, translucent material selected so that it transmits and does not substantially or inconsistently absorb near-infrared energy in the bandwidth of interest, namely, from about 740 to about 1100 nanometers. Means for providing a point source of near-infrared radiation is positioned at an upper end 53 of the tubular member 51. The near-infrared point source means at the upper end portion 53 of tube 51 is positioned so that near-infrared radiation of the predetermined wavelength emitting from the point source means will be transmitted by the tubular member 51 from the upper portion 53 to a flat bottom surface 54 of tube 51. The near-infrared point source means preferably comprises infrared emitting diode means 56.

The near-infrared apparatus of FIG. 8 includes an optical detector 58 capable of detecting near-infrared radiation positioned inside of and at the bottom end portion of the tubular member 51. Inner tube shield is positioned between detector 58 and transmitting tube 51, thereby providing an opaque mask which prevents near-infrared radiation from tube 51 from impinging directly on detector 58. A near-infrared-transparent window 59 is located in from of the optical detector 58.

The near-infrared apparatus utilizes a current modification means substantially identical to the current modification means disclosed above in connection with FIGS. 2 and 3. The optical detector 58 is connected to the input of programmable signal amplifier 60, such as the signal amplifier discussed above, by suitable electrical conducting means 33. The programmable gain amplifier 60 is provided to amplify the signal from detector 58 and input the signal to A/D converter 61. The A/D converter 61 produces an A/D conversion value which is input into the processing means 41. The processing means 41 compares the A/D conversion value with the known saturation value for the specific A/D converter. If the A/D conversion value is below the known saturation value for the A/D converter, an IRED current control circuit is caused to increase the current to the IRED by an amount, preferably, which increases the A/D conversion value to a point just below its known saturation value.

The output of amplifier 60 is also fed into a readout box 32 through conductive lines 34. The readout box 32 may have a display 36 for directly reading the percentage of fat in a test subject.

In operation, the bottom surface 54 and window 59 are positioned against a skin surface of a test subject. Substantially uniformly dispersed near-infrared radiation emerging from end 54 is transmitted into the body of the test subject to achieve optimal interactance between the body and the near-infrared radiation. During this first pass, the current supplying the IRED is modified as described above. After the optimal IRED current is determined, another near-infrared measurement is taken and the signal generated is utilized to quantitatively determine the fat content of the body, as described in U.S. Pat. No. 4,850,365, incorporated herein by reference.

Figure 9:
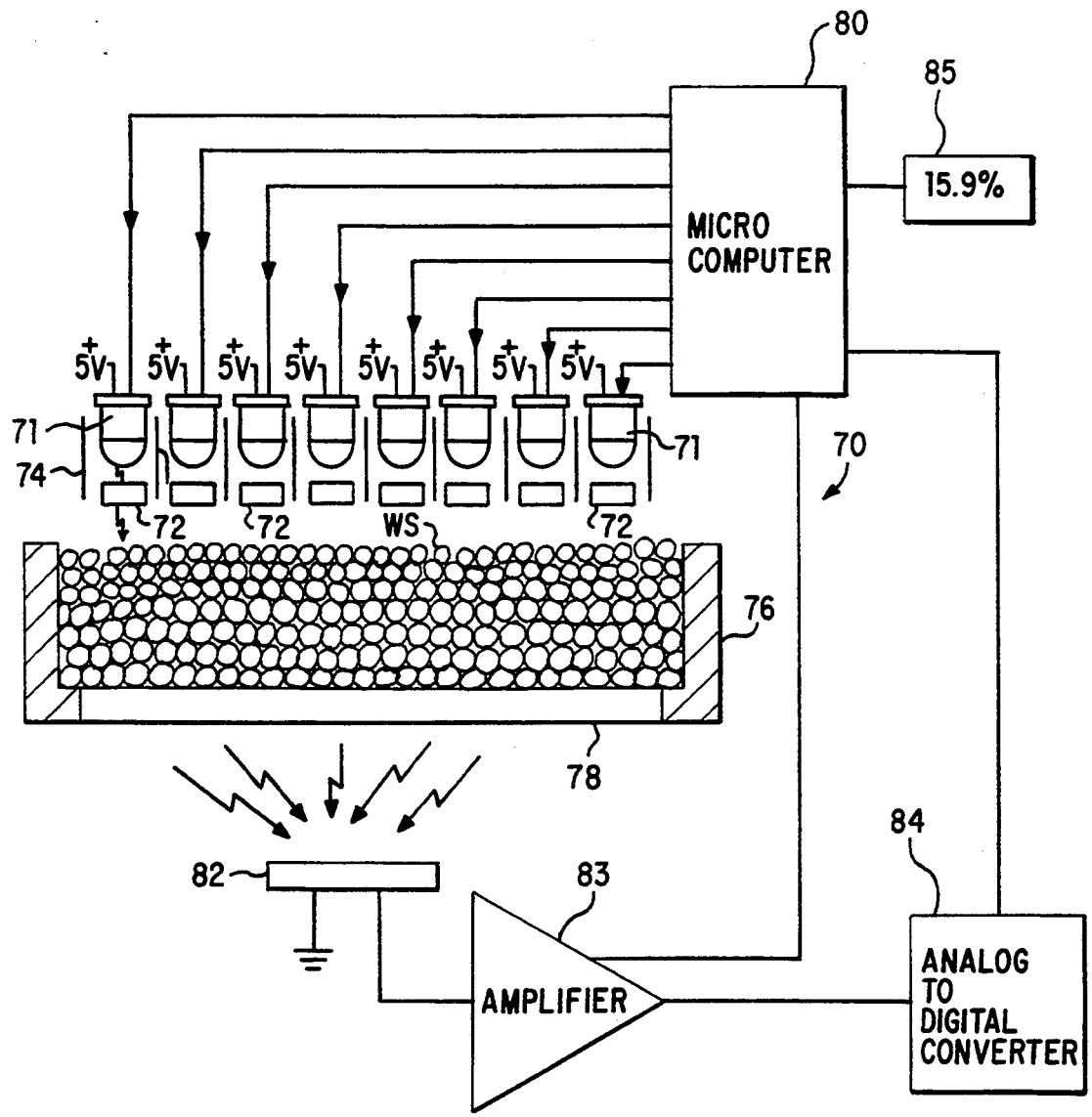
FIG. 9 illustrates an apparatus for near-infrared quantitative analysis in accordance with another embodiment of the present invention.

In accordance with another embodiment of the present invention, FIG. 9 discloses a near-infrared quantitative analysis instrument 70 for measuring a constituent present in a sample, such as the protein content in wheat, which utilizes the current modification means of the present invention. The near-infrared apparatus 70 includes a plurality of commercial IREDs 71 which are sequentially pulsed on and off by signals from a processing means 80. The processing means is programmed to allow only one of the IREDs to be turned on at a time and automatically sequences through all IREDs. The infrared light emitted from each IRED is transmitted through an accompanying narrow bandpass optical filter 72. The optical filter 72 absorbs all wavelengths of light except those near its center wavelength. Light baffles 74 positioned between each set of IREDs and narrow bandpass filters prevent the light from one IRED being transmitted through an adjacent narrow bandpass filter.

Each of the specific wavelengths are transmitted through appropriate optics (not shown), then through a wheat sample WS that is held in an opaque cup 76. The cup has a glass bottom 78 so that the light energy can pass through and impact on a silicon photodetector 82. The light impacting on the silicon detector is converted by the detector into an electrical current which is amplified by a programmable gain amplifier 83, such as the programmable gain amplifier described above. The output of the amplifier 83 is input into an analog-to-digital computer 84 and is then input into a microprocessor. The microprocessor then determines the amount of protein in each sample as described in U.S. Pat. No. 4,286,327, incorporated herein by reference, which is displayed on a digital meter 85 built into the instrument.

The analysis instrument 70 also utilizes the current modification means substantially identical to the current modification means disclosed above in connection with FIGS. 2 and 3. The photodetector 82 is connected to the input of programmable signal amplifier 83, such as the signal amplifier discussed above. The programmable gain amplifier 83 is provided to amplify the signal from detector 82 and input the signal to A/D converter 84. The A/D converter 84 produces an A/D conversion value which is input into the microprocessor. The microprocessor compares the A/D conversion value with the known saturation value for the specific A/D converter. If the A/D conversion value is below the known saturation value for the A/D converter, an IRED current control circuit is caused to increase the current to a specific IRED by an amount, preferably, which increases the A/D conversion value to a point just below its known saturation value.

In operation, a first pass is made in which the desired IRED driving currents are established for IRED, as described above. After the IRED driving currents have been established, another measurement is made and the amount of the constituent contained in the sample, i.e. protein in wheat, is determined.

Although the invention has been described in connection with preferred embodiments, it is not limited to them. For example, the current modification process of the present invention is used to modify the current to individual IREDs in the non-invasive blood glucose measurement instrument which utilizes the principle of light interactance to measure blood constituents, such as the one disclosed in U.S. Pat. No. 5,086,229, incorporated herein by reference. Modifications within the scope of the following claims will be apparent to those skilled in the art.

We claim:

1. A near-infrared quantitative analysis instrument for non-invasive measurement of a constituent of a product, said analysis instrument comprising:
   (a) introducing means including a near-infrared energy source including infrared emitting diodes for introducing near-infrared energy into a product;
   (b) detector circuit means for detecting near-infrared energy emerging from said product, said detecting means producing a signal indicative of said energy emerging from said product;
   (c) means for supplying current to each of said infrared emitting diodes in said introducing means;
   (d) current modification means for modifying the current supplied to each infrared emitting diode in response to said signal from said detector circuit means; and
   (e) processing means for calculating the electrical signal from said detector circuit means into a signal indicative of the quantity of said constituent present in said product.

2. The near-infrared analysis instrument as set forth in claim 1, wherein said detector circuit means comprises an analog-to-digital converter which generates a signal representative of the energy emerging from said product.

3. The near-infrared analysis instrument as set forth in claim 2, wherein said detector circuit means comprises a programmable gain amplifier.

4. The near-infrared analysis instrument as set forth in claim 2, wherein said analog-to-digital converter is a 12-bit analog-to-digital converter.

5. The near-infrared analysis instrument as set forth in claim 2, wherein said current modification means modifies the current to an IRED in response to the signal from said analog-to-digital converter.

6. The near-infrared analysis instrument as set forth in claim 1, wherein said current modification means comprises an infrared emitting diode current control circuit for modifying the current to an infrared emitting diode.

7. The near-infrared analysis instrument as set forth in claim 1, wherein said processing means comprises means for calculating the quantity of a blood analyte present in the blood of a subject.

8. The near-infrared analysis instrument as set forth in claim 1, wherein said processing means comprises means for calculating the amount of protein present in a wheat sample.

9. The near-infrared analysis instrument as set forth in claim 1, wherein said processing means comprises means for calculating the percentage of fat present in a body.

10. A near-infrared quantitative analysis instrument for non-invasive measurement of a blood analyte present in a body part of a subject, said analysis instrument comprising:
    (a) introducing means including a near-infrared energy source including infrared emitting diodes for introducing near-infrared energy into blood present in a body part of a subject;
    (b) detector circuit means for detecting near-infrared energy emerging from the body part, said detecting means producing a signal indicative of said energy emerging from said body part;
    (c) means for supplying current to each of said infrared emitting diodes in said introducing means;
    (d) current modification means for modifying the current supplied to each infrared emitting diode in response to said signal from said detector circuit means; and
    (e) processing means for calculating the electrical signal from said detector circuit means into a signal indicative of the quantity of said blood analyte present in the blood of the subject.

11. The near-infrared analysis instrument as set forth in claim 10, wherein said detector circuit means comprises an analog-to-digital converter which generates a signal representative of the energy emerging from said body part.

12. The near-infrared analysis instrument as set forth in claim 11, wherein said detector circuit means comprises a programmable gain amplifier.

13. The near-infrared analysis instrument as set forth in claim 11, wherein said analog-to-digital converter is a 12-bit analog-to-digital converter.

14. The near-infrared analysis instrument as set forth in claim 11, wherein said current modification means modifies the current to an IRED in response to the signal from said analog-to-digital converter.

15. The near-infrared analysis instrument as set forth in claim 10, wherein said current modification means comprises an infrared emitting diode current control circuit for modifying the current to an infrared emitting diode.

16. The near-infrared analysis instrument as set forth in claim 10, wherein said analysis instrument comprises a housing means for housing at least said introducing means and said detecting means, said housing means comprising a chamber means for enabling said body part of said subject to be exposed to said near-infrared energy, said introducing means and said detecting means being positioned about said chamber means such that near-infrared energy emitted by said introducing means is receivable by said detecting means.

17. The near-infrared analysis instrument as set forth in claim 16, wherein said analysis instrument comprises an insert means for receiving said body part of said subject and for engaging said chamber means.

18. The near-infrared analysis instrument as set forth in claim 10, wherein said analytical instrument. further comprises an energy conservation means for terminating the drain on a power supply to the instrument if a measurement isn't taken within a predetermined time period.

19. The near-infrared analysis instrument as set forth in claim 18, wherein said predetermined time period is approximately one minute.

20. A near-infrared quantitative analysis instrument for non-invasive measurement of a blood analyte present in a body part of a subject, said analysis instrument comprising:

(a) introducing means including a near-infrared energy source including infrared emitting diodes for introducing near-infrared energy into blood present in a body part of a subject;
(b) detecting means for detecting near-infrared energy emerging from the body part, said detecting means producing a signal indicative of said energy emerging from said body part;
(c) a housing means for housing at least said introducing means and said detecting means, said housing means comprising a chamber means for enabling said body part of said subject to be exposed to said near-infrared energy, said introducing means and said detecting means being positioned about said chamber means such that near-infrared energy emitted by said introducing means is receivable by said detecting means:
(d) an insert means for receiving said body part of said subject and for engaging said chamber means;
(e) means for supplying current to each of said infrared emitting diodes in said introducing means;
(f) current modification means for modifying the current supplied to each infrared emitting diode in response to said signal from said detection means; and
(g) processing means for calculating the electrical signal from said detection means into a signal indicative of the quantity of said blood analyte present in the blood of the subject.

21. A near-infrared quantitative analysis instrument for non-invasive measurement of a blood analyte present in a body part of a subject, said analysis instrument comprising:
(a) introducing means including a near-infrared energy source including infrared emitting diodes for introducing near-infrared energy into blood present in a body part of a subject;
(b) detector circuit means for detecting near-infrared energy emerging from the body part, said detecting means producing a signal indicative of said energy emerging from said body part;
(c) means for storing an optical signature comprised of optical data corresponding to the body part and/or blood within the body part at a given time;
(d) means for generating a real time optical signature corresponding to stored optical data which makes up the optical signature; and
(e) processing means for comparing the stored optical signature with the real time optical signature, whereby correspondence of the stored optical signature and the real time optical signature results in a condition permitting an analysis to be performed by the instrument.

* * * * *